United States Patent
Sarkinen et al.

(10) Patent No.: US 7,927,326 B2
(45) Date of Patent: Apr. 19, 2011

(54) RESIDUAL ENERGY RECOVERY IN A DRUG DELIVERY DEVICE

(75) Inventors: Scott A. Sarkinen, Greenfield, MN (US); James M. Haase, Maplewood, MN (US); Ronald L. Mezera, Lake Elmo, MN (US); Christian Peclat, Neuchatal (CH)

(73) Assignee: Medtronic, Inc., Minneapolis, MN (US)

( * ) Notice: Subject to any disclaimer, the term of this patent is extended or adjusted under 35 U.S.C. 154(b) by 808 days.

(21) Appl. No.: 11/796,622

(22) Filed: Apr. 27, 2007

(65) Prior Publication Data

US 2008/0267796 A1 Oct. 30, 2008

(51) Int. Cl.
*A61M 1/00* (2006.01)
*H01H 47/00* (2006.01)
*F04B 17/04* (2006.01)
*H02J 7/00* (2006.01)

(52) U.S. Cl. ............... 604/891.1; 604/152; 361/159; 361/156; 417/411; 307/109; 320/166

(58) Field of Classification Search .............. 417/44.1, 417/411, 53; 310/339, 399; 604/65, 66, 604/67, 131, 151, 152, 153, 154, 155, 890.1, 604/891.1; 361/159, 156, 155; 307/109; 320/166

See application file for complete search history.

(56) References Cited

U.S. PATENT DOCUMENTS

| | | | | |
|---|---|---|---|---|
| 4,604,090 | A | * | 8/1986 | Reinicke .................. 604/118 |
| 5,036,422 | A | * | 7/1991 | Uchida et al. ............. 361/159 |
| 5,121,314 | A | | 6/1992 | Cathell et al. |
| 5,318,521 | A | | 6/1994 | Slettenmark |
| 5,527,307 | A | | 6/1996 | Srisathapat et al. |
| 6,087,863 | A | * | 7/2000 | Aflatouni ................. 327/111 |
| 6,227,818 | B1 | | 5/2001 | Falk et al. |
| 6,398,511 | B1 | * | 6/2002 | French et al. ............. 417/53 |
| 6,458,164 | B1 | * | 10/2002 | Weiss .................... 623/3.27 |
| 6,488,652 | B1 | | 12/2002 | Weijand et al. |
| 6,580,177 | B1 | * | 6/2003 | Hagood et al. ........... 290/1 R |
| 6,589,205 | B1 | * | 7/2003 | Meadows ................. 604/67 |
| 6,595,756 | B2 | | 7/2003 | Gray et al. |
| 6,770,067 | B2 | | 8/2004 | Lorenzen et al. |
| 6,865,417 | B2 | * | 3/2005 | Rissmann et al. .......... 607/5 |
| 7,070,577 | B1 | * | 7/2006 | Haller et al. ............. 604/131 |
| 7,075,077 | B2 | | 7/2006 | Okuda et al. |
| 2002/0051368 | A1 | | 5/2002 | Ulinski et al. |
| 2002/0171297 | A1 | | 11/2002 | Talbot et al. |

(Continued)

FOREIGN PATENT DOCUMENTS

DE 102 37 779 3/2004

(Continued)

OTHER PUBLICATIONS

B.E. Strickland et al., A solid state modulator using energy recovery to deliver 20 kVA to an inductive load from a 2.5 kJ/s power source, 1990 IEEE.*

*Primary Examiner* — Devon C Kramer
*Assistant Examiner* — Nathan Zollinger
(74) *Attorney, Agent, or Firm* — Kinney & Lange, P.A.

(57) ABSTRACT

An implantable drug delivery device includes a pump motor that is driven by electrical energy from a storage capacitor. At the end of each pump delivery cycle, electrical energy stored in the pump motor is recovered and returned to the storage capacitor, so that it can be used in subsequent delivery cycles.

19 Claims, 2 Drawing Sheets

U.S. PATENT DOCUMENTS

| | | | |
|---|---|---|---|
| 2002/0173774 A1* | 11/2002 | Olsen | 604/891.1 |
| 2004/0059315 A1* | 3/2004 | Erickson et al. | 604/890.1 |
| 2006/0047367 A1 | 3/2006 | Rogers et al. | |
| 2006/0119300 A1* | 6/2006 | Armstrong | 318/254 |
| 2008/0008609 A1* | 1/2008 | Pate et al. | 417/415 |
| 2008/0139996 A1* | 6/2008 | Bowman et al. | 604/67 |
| 2009/0201620 A1* | 8/2009 | Gray et al. | 361/159 |
| 2009/0225574 A1* | 9/2009 | Fornage | 363/123 |
| 2009/0261764 A1* | 10/2009 | Hirata | 318/400.29 |

FOREIGN PATENT DOCUMENTS

| | | |
|---|---|---|
| WO | WO 99/23746 | 5/1999 |

* cited by examiner

RESIDUAL ENERGY RECOVERY IN A DRUG DELIVERY DEVICE

CROSS-REFERENCE TO RELATED APPLICATION(S)

Reference is made to co-pending application entitled "IMPLANTABLE DRUG DELIVERY DEVICE WITH PROGRAMMABLE RATE CAPACITOR CHARGE CONTROL", Ser. No. 11/796,604, which is hereby incorporated by reference.

BACKGROUND

The present invention relates to implantable medical devices. In particular, the present invention relates to a charging of a storage capacitor from a battery and subsequently delivering stored energy from the storage capacitor to a pump motor.

Implantable drug delivery devices are used to provide patients with long-term dosage or infusion of a drug or other therapeutic agent. Implantable drug delivery devices may be categorized as either passive or active devices.

Passive drug delivery devices typically rely upon a pressurized drug reservoir to deliver the drug. The reservoir may be filled using a syringe. The drug is then delivered to the patient using force provided by the pressurized reservoir.

Active drug delivery devices include a pump or metering system to deliver the drug into the patient's system. The pump is electrically powered to deliver the drug from a reservoir through a catheter to a selected location within the patient's body. The pump typically includes a battery as its power source for both the pump and for the electronic circuitry used to control flow rate of the pump and to communicate through telemetry to an external device to allow programming of the pump.

Battery life is an important consideration for all implantable medical devices. With an implantable drug delivery device, efficiency of the driver circuitry that powers the pump motor is an important consideration. In one type of driver configuration, the pump motor is driven from electrical energy stored by a storage capacitor. The capacitor serves as a low-impedance, short-term energy reservoir to deliver sufficient power to the motor during assertion. During operation, the motor will be asserted periodically for a short period of time to provide a pulse flow of the drug, with longer period until the next assertion.

The efficiency of the driver circuitry can have an important effect on the lifetime of the battery, overall volume of the device including battery size, capacitor size, and size of the circuitry required, and on the overall cost of the device. Considerations in the efficiency of the driver include efficiency of charging the storage capacitor, and efficiency of delivering energy stored in the storage capacitor to the pump motor.

SUMMARY

An implantable drug delivery device increases energy efficiency by recovering energy at the end of each pump delivery cycle. The implantable drug delivery device includes a battery, a storage capacitor, a pump motor, a circuit for charging the storage capacitor from the battery, and a circuit for delivering electrical energy stored in the storage capacitor to the motor. At the end of a delivery cycle of the pump, electrical energy stored in the pump motor is recovered and returned to the storage capacitor for use in subsequent delivery cycles.

DETAILED DESCRIPTION

Figure 1:
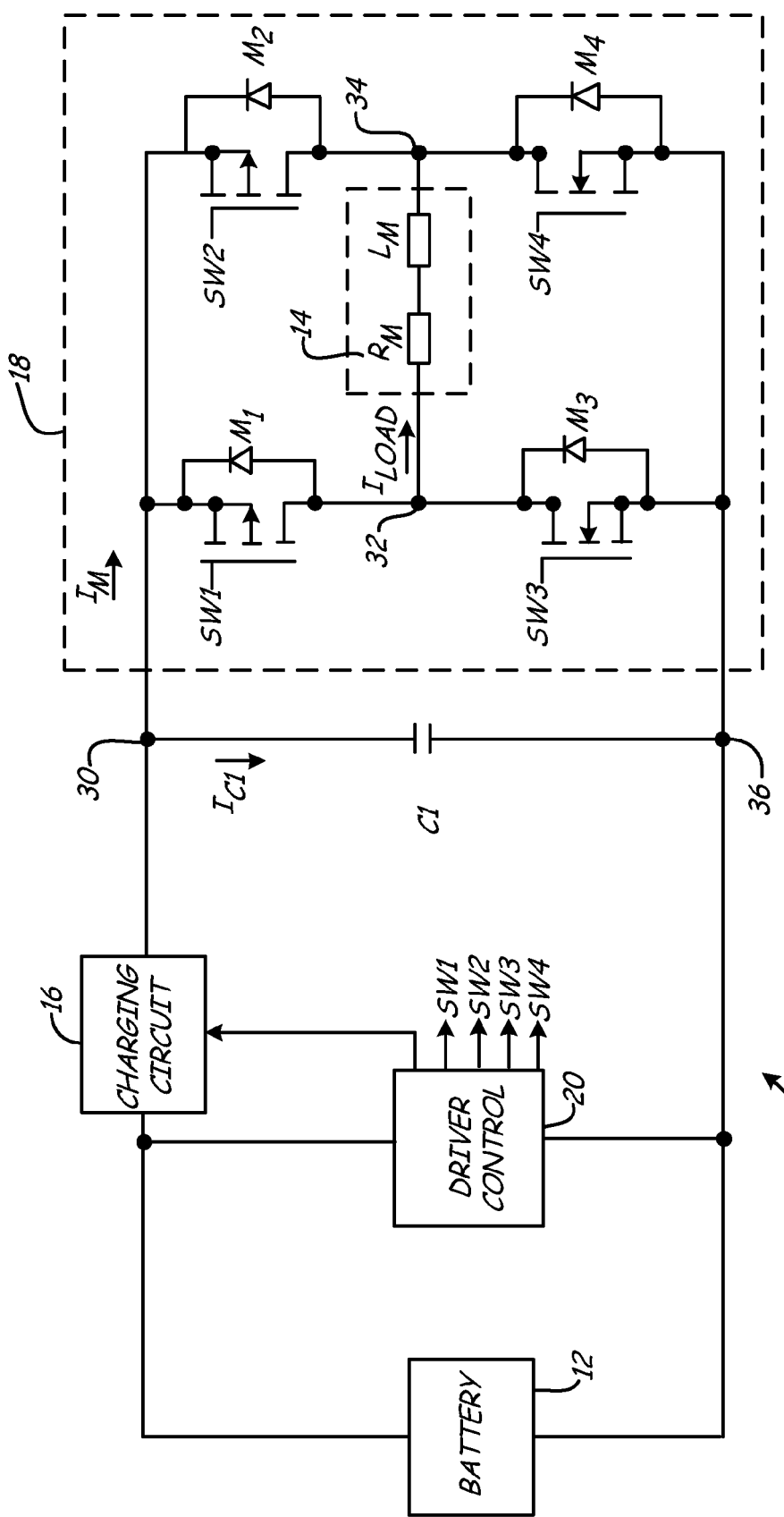
FIG. 1 is a schematic diagram showing an implantable drug delivery device with a motor control circuit that delivers electrical energy from a storage capacitor to a pump motor, recovers electrical energy stored in the pump motor at the end of a cycle, and returns the electrical energy to the storage capacitor.

FIG. 1 shows implantable drug delivery device 10, which includes battery 12, pump motor 14, charging circuit 16, motor control circuit 18, driver control 20, and storage capacitor $C_1$. Battery 12 acts as a power source that provides all the electrical energy for operation of implantable drug delivery device 10. Motor 14 is, in one embodiment, a solenoid type pump. As shown in FIG. 1, motor 14 represents a load having a real component $R_M$ and an inductive component $L_M$. When motor 14 is asserted, a solenoid coil is energized, which produces an electromagnetic field causing an actuator such as a solenoid plunger to move. Motor 14 may also include a spring bias, which returns the actuator to its original position when the solenoid coil is no longer energized.

Motor 14 is typically asserted or energized for a relatively short time period, with a relatively long period between successive assertions. The delivery rate of the pump will depend on the period of time between successive assertions of motor 14 to produce a pump stroke. Assertion time of motor 14 may be on the order of milliseconds (e.g. 5 milliseconds) and the period between motor assertion will vary with delivery rate and may be on the order of several seconds (e.g. 3 seconds).

Motor 14 is isolated from battery 12 by a motor driver formed by charging circuit 16, motor control circuit 18, driver control 20, and storage capacitor $C_1$. Motor 14 is driven by energy stored in storage capacitor $C_1$, rather than directly from battery 12. As a result, a low impedance load presented by motor 14 is not directly connected to battery 12, and therefore does not cause a decrease or droop in battery voltage each time a motor assertion occurs. Stability of the battery voltage is important to proper functioning of the electrical circuitry of device 10.

Charging circuit 16 may take a number of different forms. In one embodiment, charging circuit 16 includes electronic switches, under the control of driver control 20, which are operated to provide improved efficiency in delivery of charging current from battery 12 to storage capacitor $C_1$. One example of a suitable charging circuit is shown in the previously mentioned co-pending application Ser. No. 11/796,604, which is incorporated by reference.

The delivery of current from storage capacitor $C_1$ to pump motor 14 is controlled by motor control circuit 18 in response to switching signals received from driver control 20. After storage capacitor $C_1$ has been charged, driver control 20 provides switch control signals Sw1-Sw4 to electronic switches $M_1$-$M_4$ of motor control circuit 18. As a result, pump motor 14 is asserted for a time period $t_{ON}$ that is sufficient to drive the solenoid plunger or actuator to the end of its stroke.

In the embodiment shown in FIG. 1, switches M-$M_4$ of motor control circuit 18 are connected in an H-bridge configuration. Switch Sw1 is connected between capacitor terminal 30 and H-bridge node 32. Switch Sw2 is connected between capacitor terminal 30 and H-bridge node 34. Pump motor 14 is connected between H-bridge nodes 32 and 34.

Switch Sw3 is connected between H-bridge node 32 and capacitor terminal 36. Similarly, switch $M_4$ is connected between H bridge node 34 and capacitor terminal 36.

This H-bridge configuration provides improved efficiency by delivering energy from storage capacitor $C_1$ to pump motor 14 during motor assertion period $t_{ON}$ and by retrieving residual energy and returning that unused residual energy to storage capacitor $C_1$ at the end of each pump stroke during energy recovery period $t_{DISCHARGE}$. Only a fraction of the electric energy delivered from storage capacitor $C_1$ during motor assertion period $t_{ON}$ is required to trigger a specific action of solenoid pump motor 14. Part of the energy from storage capacitor $C_1$ is still stored in the magnetic field surrounding the solenoid (i.e. in conductive component $L_M$) after the mechanical action of pump motor 14 has been performed. The actual current $I_{LOAD}$ through inductive component $L_M$ cannot instantaneously change when the motor assertion period $t_{ON}$ ends. It can, however, be redirected back to storage capacitor $C_1$ so that the energy is recovered.

Figure 2:
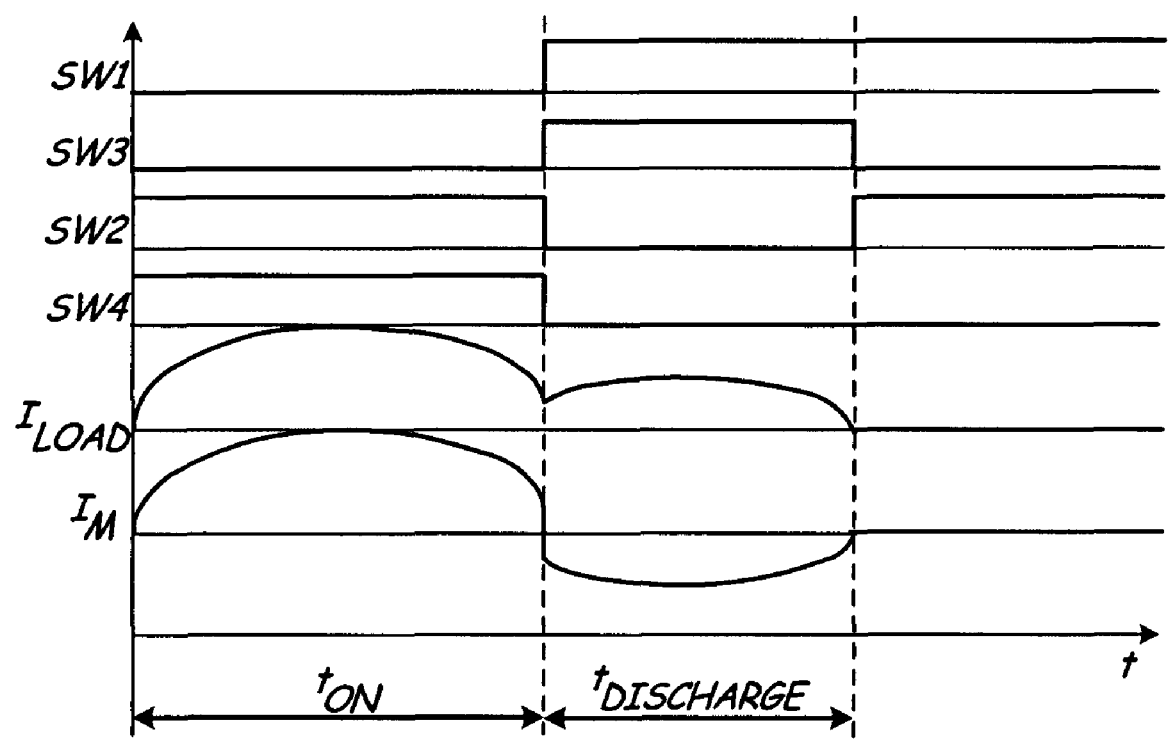
FIG. 2 is a timing diagram illustrating operation of the device in FIG. 1 during motor assertion and subsequent energy recovery.

The operation of motor control circuit 18 is further illustrated by FIG. 2, which shows the switch control signals to the gates of switches $M_1$-$M_4$, along with the load current $I_{LOAD}$ and the motor current $I_M$. At the beginning of motor assertion, switches $M_1$ and $M_4$ are turned on, while switches $M_2$ and $M_3$ are turned off. As a result, motor current $I_M$ flows from storage capacitor terminal 30, through switch $M_1$, from node 32 through $R_M$ and $L_M$ to node 34, and through switch $M_4$ to storage capacitor terminal 36. During the assertion period $t_{ON}$, load current $I_{LOAD}$ equals motor current $I_M$ in polarity, as shown in FIG. 2. At the end of assertion period $t_{ON}$, switches $M_1$ and $M_4$ are opened, and switches $M_2$ and $M_3$ are closed to begin energy recovery period $t_{DISCHARGE}$. Depending on switch timing, the diodes associated with $M_2$ and $M_3$ may turn on before the transistors of $M_2$ and $M_3$ turn on. The load current $I_{LOAD}$ is now in the opposite direction of motor current $I_M$, which causes electrical energy to be fed back to storage capacitor $C_1$. With switches $M_2$ and $M_3$ closed, a current path is established from storage capacitor terminal 36, through $M_3$ to node 32, through $R_M$ and $L_M$ to node 34, and through switch $M_2$ to storage capacitor terminal 30. When $I_{LOAD}$ reaches zero, switches $M_2$ and $M_3$ are also opened so that pump motor 14 is isolated from storage capacitor $C_1$.

Because a motor control circuit 18 recovers residual energy and returns it to storage capacitor $C_1$, improved efficiency is achieved. This improvement can be on the order of 10%. Without the recovery of the residual energy remaining in pump motor 14 at the end of the assertion period, the energy will be dissipated in the form of heat, rather than being available for reuse.

The timing of operation of switches of $M_1$-$M_4$ is based upon an assertion period $t_{ON}$ that will result in a full pump stroke. Driver control 20 may include sensing circuitry to detect when the end of assertion period $t_{ON}$ (i.e. the end of the pump stroke) occurs. Alternatively, the time duration of assertion period $t_{ON}$ may be determined empirically through testing and stored as an operating parameter of driver control 20.

Similarly, detection of a change in direction of flow of current $I_{LOAD}$ at the end of energy recovery period $t_{DISCHARGE}$ may be used by said driver control 20 to determine when to turn off switches $M_2$ and $M_3$. A small resistance in the current path of current $I_{LOAD}$ or current $I_M$ may be used to develop a voltage feedback signal to driver control 20.

Although an H-bridge configuration has been illustrated for motor control circuit 18, other known switching configurations may be used. The switching configuration should provide a current path at the end of the assertion period, to return energy stored in inductive component $L_M$ of pump motor 14 to storage capacitor $C_1$.

With the present invention, implantable devices using motors that retain residual energy can be operated with smaller sized batteries, or can have a longer usable life because of the improved efficiency in transfer of energy from the storage capacitor to the motor.

Although the present invention has been described with reference to preferred embodiments, workers skilled in the art will recognize that changes may be made in form and detail without departing from the spirit and scope of the invention.

The invention claimed is:

1. An implantable drug delivery device comprising:
 a battery;
 a storage capacitor;
 a solenoid pump that produces a pump stroke of an actuator during a motor assertion period to pump a drug or therapeutic agent into a patient;
 a charging circuit connected between the battery and the storage capacitor for charging the storage capacitor from the battery and for isolating the solenoid pump from the battery; and
 a motor control circuit for delivering electrical energy stored in the storage capacitor to the solenoid pump during the motor assertion period to produce the pump stroke and for recovering electrical energy stored in the solenoid pump at an end of the pump stroke during an energy recovery period following the motor assertion period and returning the electrical energy recovered to the storage capacitor.

2. The device of claim 1, wherein the solenoid pump is connected between a first node and a second node, and wherein the motor control circuit comprises an H-bridge switching circuit including:
 a first field effect transistor (FET) switch connected between a first terminal of the storage capacitor and the first node;
 a second FET switch connected between the first terminal and the second node;
 a third FET switch connected between the first node and a second terminal of the storage capacitor; and
 a fourth FET switch connected between the second node and the second terminal of the storage capacitor.

3. The device of claim 2, wherein the motor control circuit further comprises:
 a switch control for providing switch control signals to cause the first and fourth FET switches to be on and the second and third FET switches to be off when delivering electrical energy to the solenoid pump during the motor assertion period, and to cause the first and fourth FET switches to be off and the second and third FET switches to be on when recovering electrical energy stored in the solenoid pump and returning the electrical energy recovered to the storage capacitor during the energy recovery period.

4. An implantable drug delivery device comprising:
 a battery;
 a electromechanical pump motor that includes a solenoid coil that is energized during a motor assertion period to cause an actuator to move through a pump stroke that pumps a drug or therapeutic agent into a patient; and
 a motor driver including a storage capacitor, a charging circuit for charging the storage capacitor from the battery and for isolating the battery from the pump motor, and a switching circuit for driving the pump motor with electrical energy supplied from the storage capacitor to the solenoid coil during a motor assertion period, and for recovering energy stored in the pump motor and returning the energy recovered to the storage capacitor during an energy recovery period.

5. The device of claim 4, wherein the switching circuit causes current to flow in a first direction from the storage capacitor to the pump motor during a motor assertion period and causes current to flow in a second direction from the pump motor to the storage capacitor during an energy recovery period following the motor assertion period.

6. The device of claim 5, wherein the pump motor is connected between a first node and a second node, and wherein the switching circuit comprises an H-bridge switching circuit including:
a first field effect transistor (FET) switch connected between a first terminal of the storage capacitor and the first node;
a second FET switch connected between the first terminal and the second node;
a third FET switch connected between the first node and a second terminal of the storage capacitor; and
a fourth FET switch connected between the second node and the second terminal of the storage capacitor.

7. The device of claim 6, wherein the motor driver further comprises:
a control for providing switch control signals to cause the first and fourth FET switches to be on and the second and third FET switches to be off during the motor assertion period, and to cause the first and fourth FET switches to be off and the second and third FET switches to be on during the energy recovery period.

8. The device of claim 5, wherein current flow through the pump motor is in the same direction during both the motor assertion period and the energy recovery period.

9. The device of claim 1, wherein the motor control circuit detects occurrence of an end of the pump stroke and initiates the energy recovery period.

10. The device of claim 1, wherein the motor control circuit ends the motor assertion period at a predetermined time duration and initiates the energy recovery period.

11. The device of claim 1, wherein the motor control circuit ends the energy recovery period so that the solenoid pump is isolated from the storage capacitor when current flow from the solenoid pump to the storage capacitor reaches zero.

12. The device of claim 1, wherein the motor control circuit ends the energy recovery period in response to detection of a change in direction of load current flow through the solenoid pump.

13. An implantable drug delivery device comprising:
a battery;
a storage capacitor;
a solenoid pump having a solenoid coil and an actuator that moves through a pump stroke in response to an electromagnetic field produced by the solenoid coil to pump a drug or therapeutic agent into a patient;
a charging circuit between the battery and the storage capacitor for charging the storage capacitor from the battery and for isolating the battery from the solenoid pump; and
an H-bridge switching circuit connected between the capacitor and the solenoid coil for discharging stored electrical energy from the storage capacitor to the solenoid coil until the actuator stops moving at an end of the pump stroke, and for recovering electrical energy from the pump motor and returning the electrical energy recovered to the storage capacitor after the actuator stops at an end of the pump stroke.

14. The device of claim 13,
wherein the H-bridge switching circuit causes current to flow in a first direction from the storage capacitor to the solenoid pump during a motor assertion period; and
wherein the H-bridge switching circuit causes current to flow in a second direction from the solenoid pump to the storage capacitor during an energy recovery period following the motor assertion period.

15. The device of claim 14, wherein current flow through the solenoid coil is in the same direction during both the motor assertion period and the energy recovery period.

16. The device of claim 15, wherein the H-bridge switching circuit comprises:
a first field effect transistor (FET) switch connected between a first terminal of the storage capacitor and a first node;
a second FET switch connected between the first terminal and a second node;
a third FET switch connected between the first node and a second terminal of the storage capacitor; and
a fourth FET switch connected between the second node and the second terminal of the storage capacitor.

17. The device of claim 16, wherein the solenoid coil is connected between the first node and the second node.

18. The device of claim 17, wherein the first and fourth FET switches are turned on and the second and third FET switches are turned off during the motor assertion period.

19. The device of claim 18, wherein the first and fourth FET switches are turned off and the second and third FET switches are turned on during the energy recovery period.

* * * * *